United States Patent [19]
Dondlinger

[11] Patent Number: 5,265,724
[45] Date of Patent: Nov. 30, 1993

[54] MEDICAL NEEDLE DISPOSAL PACKAGE

[76] Inventor: Steven C. Dondlinger, 5513 Knoll Dr., Edina, Minn. 55436

[21] Appl. No.: 978,419

[22] Filed: Nov. 18, 1992

Related U.S. Application Data

[63] Continuation-in-part of Ser. No. 878,298, May 6, 1992.

[51] Int. Cl.$^5$ ............................................. B65D 85/24
[52] U.S. Cl. ................................ 206/366; 206/365; 206/813; 220/8
[58] Field of Search ............... 206/366, 365, 813, 523; 220/8, 555

[56] References Cited

U.S. PATENT DOCUMENTS

| | | | |
|---|---|---|---|
| 4,844,249 | 7/1989 | Coulombe | 206/366 |
| 4,936,449 | 6/1990 | Conard et al. | 206/366 |
| 5,007,535 | 4/1991 | Meseke et al. | 206/366 |
| 5,020,665 | 6/1991 | Bruno | 220/555 |
| 5,024,326 | 6/1991 | Sandel et al. | 206/366 |
| 5,038,929 | 8/1991 | Kubofcik | 206/523 |

FOREIGN PATENT DOCUMENTS 9006784 6/1990 PCT Int'l Appl. ................ 206/366

Primary Examiner—William I. Price
Attorney, Agent, or Firm—Hugh D. Jaeger

[57] ABSTRACT

A medical needle disposal package for disposing of needles, such as surgical needles, IV needles, syringe needles, lancets, and other like sharp surgical devices. A package with hard sides, a hard bottom and sticky tape on the bottom and/or sides, contains STYROFOAM-like material. The used surgical needles or devices are stuck into the STYROFOAM. The package provides that a needle can be stuck into the STYROFOAM with one hand. At a latter time, the package and needles are disposed of by accepted surgical waste disposal procedures. The package can also be provided with an engagable top. An alternative embodiment illustrates compartments at the end or ends or sides of the package for reusable sharps storage including one-handed accessibility to the stored sharps during a medical procedure.

20 Claims, 7 Drawing Sheets

MEDICAL NEEDLE DISPOSAL PACKAGE

CROSS REFERENCES TO CO-PENDING APPLICATIONS

This patent application is a continuation-in-part of U.S. Ser. No. 07/878,298, filed May 6, 1992, entitled "Medical Needle Disposal Package".

BACKGROUND OF THE INVENTION

1. Field of the Invention

The present invention pertains to a disposable medical package, and more particularly, pertains to a disposable medical package for engaging of surgical needles or surgical instruments for later disposal.

2. Description of the Prior Art

Prior art problems of disposal of needles have been that the needles are left lying on trays, such as IV trays, causing accidental sticks, which then exposes an individual to the AIDS virus or other infectious organisms.

Further, disposing of needles has been a two-hand operation of trying to insert the needle back into the cap, and this has always been of concern of accidental sticks which exposes one to the AIDS virus or other infectious organisms, and also, used needles have either been left lying in the open or stuck into other objects, such as mattresses.

Prior art devices in general have not provided an area for reusable sharps or their covers.

The present invention overcomes the disadvantages of the prior art by providing a one-handed needle disposal process and safe location for used needles, such as on disposable trays. An area for storage of reusable sharps is also provided.

SUMMARY OF THE INVENTION

The general purpose of the present invention is a medical needle disposal package for storing of used needles and later disposal of used needles.

According to one embodiment of the present invention, there is provided a medical needle disposal package, including a block of STYROFOAM surrounded by hard sides and a hard bottom. A top can be provided for engaging onto the package for later disposition of the package. Appropriate locking members can also be provided, providing that the package cannot be reopened for any reason, so as to protect the environment. The package and the contents could then be either incinerated or disposed of at a sanitary landfill. A sticky material can be provided on the bottom or about the sides of the disposal package for engaging on an IV tray or other suitable medical table or medical appliance, further providing for one-handed operation of disposing of needles into the package.

Another embodiment of the present invention provides a medical needle disposal package including a block of STYROFOAM surrounded by hard sides, a hard bottom and compartmentalized chambers adjacent to and on opposing sides of the STYROFOAM block. These compartments include areas for storage of needle caps, needle sheaths, needles and the like.

The device is designed for more specific procedural uses. The device is designed with a size and shape to fit on and in specific medical procedure trays, such as trays for insertion of central venous pressure and arterial lines, as well as epidural and spinal trays. Its size and shape allows it to fit handily into certain areas already on these trays allowing it as an addition to the package either prior to use or during, e.g., unused areas on the trays were studied and measured, as well as comparing the size, type and number of sharps on each tray. For example: all of the trays mentioned contain at least 4, but not more than 7 sharps and most are 1½ to 2 inches in length. Sizes and shapes of needle caps and sheaths used to cover needles was also used in the design. The fact that the minimum depth of procedure trays is approximately 1⅛" has also been taken into account in the design, although it is the intention that the device can be used outside procedure trays as well. The device contains compartments designed to hold sharps for reuse ("reuse" here means during one procedure on the same patient). The size and design of these compartments is entirely based on the shape and size of items found on the above-mentioned trays. For example, protective caps for needles consist of only two external shapes (although the size may vary); a cap which has external square shaped edges or a sheath which is round externally. It is the intention for this device to incorporate various combinations and sizes of these two basic shapes for compartments. Note three types of compartments: 1) Preshaped for the size and shape of the needle cap, e.g., square or round. 2) Expandable area with vertical ridges on the interior which can adjust and friction hold by expanding against the foam compartment. The ridges give vertical support to a standing ready for reuse sharps. These ridges are spaced at various distances in order to hold various sizes of sheaths of sharps. 3) Foam compartment—for discard of sharps after final use.

It is important to note that it is very common to reuse sharps with the mentioned trays, especially when difficulty performing the procedure takes place. Current use of the trays as above consists of dropping sharps during and after us randomly onto the tray. Chance allows sharps to end up in two dangerous positions: 1) Sticking up (the heavy, non-sharp end often goes into a groove or channel of the tray); or 2) falling into a channel or groove of the tray. Both positions add risk whenever the hand returns to pick-up a sharp for reuse or to pick-up another items or to search for what is needed next as sharps lay randomly on the tray. At the end of the procedure it is more the rule that contaminated sharps are lying at random on the tray—some in grooves some pointing up partially. One must then often pick up each sharp individually for disposal or carry the tray to a large sharps container.

The device also has three primary and simultaneous uses: 1) It holds sharps in an organized fashion for reuse. These reused sharps and/or their caps or sheaths are held in compartments specifically designed for the shape and size of the sharp and/or its cap or sheath. In this way, it serves as an organizer for sharps. 2) The shape of the compartments allow a firm hold on needle caps and sheaths. This allows a one-handed capping and uncapping of needles which is important in safety and reuse. 3) A foam discard area for sharps, which will not be reused and holds them firmly and safely in place. Note the number and size of compartments varies and is based on procedure performed; however, the concept remains the same.

The compartments allow the device to be used in both sterile and non-sterile settings (e.g., when used on a sterile tray it will need to be sterile; however, if used on a surface which is not sterile all sharps can still be reused if they only touch their sterile caps or sheaths while being held in the device.) A sharp buried in the foam is not intended to be reused in any way.

The compartments are designed with a size and depth to hold sharps in a stable and ready position for easy one-handed reuse until disposal into the foam. The compartments also serve another function. The size and shape is such that needle caps will frictionally fit (pushed in so far, they will not easily come out), so as to allow one-handed needle capping and uncapping, as well as one-handed needle changing for a syringe. Needle caps often have a square configuration with four ridges. The square sharp compartment prevents needle caps from turning as syringes are turned. The size of the sharp compartments can be custom sized to accommodate a variety of needle cap sizes. The size of the device is designed with the intention of an optimal fit in most procedure trays (e.g., arterial line, epidural, cvp, etc.). Its size allows room to be used in unspecified areas of these trays, as well as allowing it to be easily packaged with these trays. Its size also allows an easy fit through the open hole of most sharps dispensers. The color of the medical disposal is intentionally bright in order to call attention to danger. A separate bright color can be used for non-sterile use, where sharp slots are only used for holding needle caps. Thickness of walls of the device allows foam to be more compact, which allows a firmer hold of "buried sharps" and also prevents sharp penetration.

The size of the medical disposal package is small enough to allow carriage of several in the pocket of a surgical gown so that a user or person can be assured of the availability of the device wherever he or she may be.

Currently, all sharps disposal boxes contain a significantly larger plastic mass from disposable syringes alone than from only sharps. With the invented device, syringes can be disposed of in the regular trash further decreasing the plastic mass (non-hazardous) medical waste. This would help to alleviate the growing hospital cost related to disposal of medical waste.

Another embodiment discloses a medical disposal package having built-in integral compartments which replicate the interior of a needle cap so that a needle may be stored for reuse without having an intermediary needle cap. Built-in integral sheaths also replicate the interior of a sheath, thus eliminating the need for an intermediary sheath. Significant aspects and features of the present invention include a medical needle disposal package which provides a soft, cellular type of material, such as STYROFOAM, which needles or other surgical devices can be easily pushed in to and also readily retained within the material.

Another significant aspect and feature of the present invention is a medical needle disposal package with STYROFOAM which provides for one-handed operation.

A further significant aspect and feature of the present invention is a medical disposal package for needles or like surgical instruments, which can be disposed of either through incineration, sanitary landfill, or other suitable processes.

Another significant aspect and feature of the present invention is that the medical disposal package can decrease the size of plastic trays by organizing sharps into a smaller area.

Another significant aspect and feature of the present invention is that the medical disposal package can decrease medical waste by allowing plastic trays to more easily be thrown into regular trash, and not into a dedicated medical waste box for disposal of sharps.

Another significant aspect and feature of the present invention is the inclusion of holding areas for reusable items adjacent to the foam structure, such as sharps, sharp sheaths, syringe caps, syringes, surgical blades, or the like.

Another significant aspect and feature of the present invention is a chamber for frictional engagement of needle caps.

Another significant aspect and feature of the present invention is a compartmentalized chamber having an expandable wall for the frictional engagement of syringe sheaths.

Another significant aspect and feature of the present invention is the storage of needles in a compartmentalized chamber.

Another significant aspect and feature of the present invention is an integral built-in cap.

Another significant aspect and feature of the present invention is an integral built-in sheath.

Having thus described the embodiments of the present invention, it is a principal object hereof to provide a medical needle disposal package.

One object of the present invention is to provide a medical needle disposal package to prevent accidental sticks and potential exposure to the AIDS virus or other infectious organisms.

Another object of the present invention is to provide a medical needle disposal package which provides for one-handed operation and is economical enough to be at all sites of all needle or instrument usage which could possibly cause an accidental stick or cut, exposing one to the AIDS virus or other infectious organisms.

A further object of the present invention is a medical disposal package which serves the purpose to reduce medical waste.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
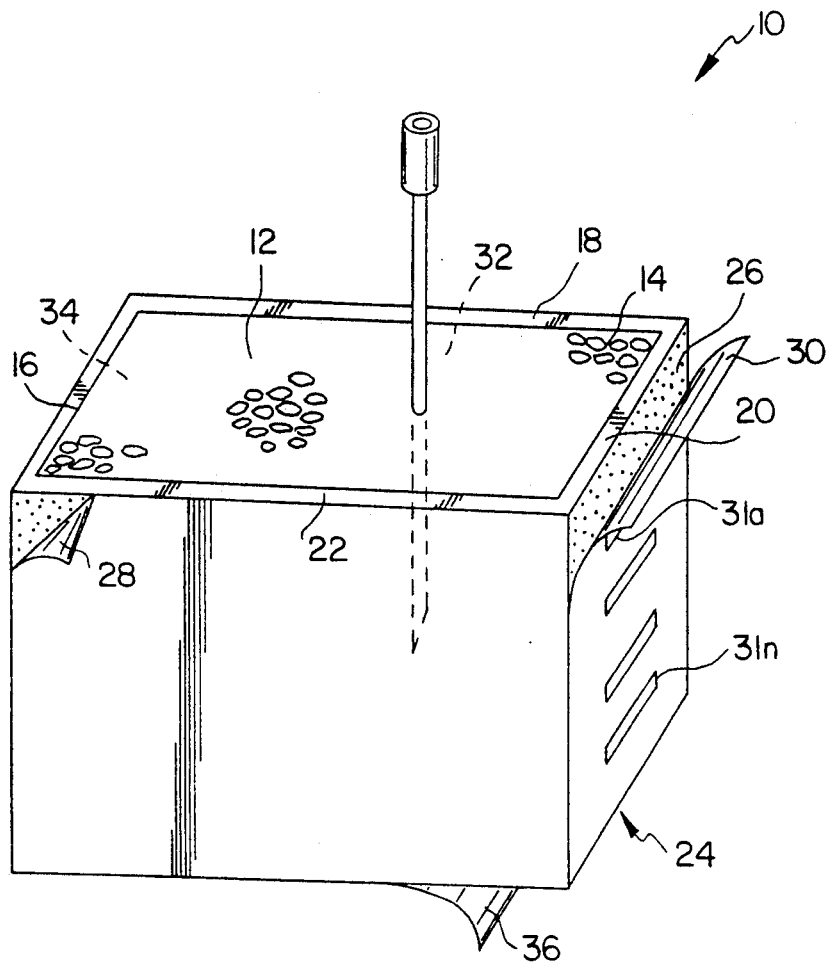
FIG. 1 illustrates the medical needle disposal package and a needle engaged within the package.

FIG. 1 illustrates a perspective view of a medical needle disposal package 10 including a block or like member 12 of soft or pliable cellular material, such as STYROFOAM 14, by way of example and for purposes of illustration only and not to be construed as limiting of the present invention, engaged by four hard sides 16, 18, 20 and 22, and a bottom 24. Other materials, such as polystyrenes, polyurethanes or any other suitable polymers, which would functionally engage a needle in a firm position. In this view the sides 16-22 and the bottom 24 are coated with an adhesive 26, or in the alternative, are covered with a double-sided adhesive tape or the like, one side of which adheres to the sides 16-22 and the bottom 24. Protective peel-away sheets 28, 30, 32, 34 and 36 overlay the adhesive 26 on the sides 16-22 and the bottom 24, and are peeled away as illustrated so that one or more of the planar surfaces of the sides 16-22 and the bottom 24 can be adhesively secured to a surgical table or tray.

Figure 2:
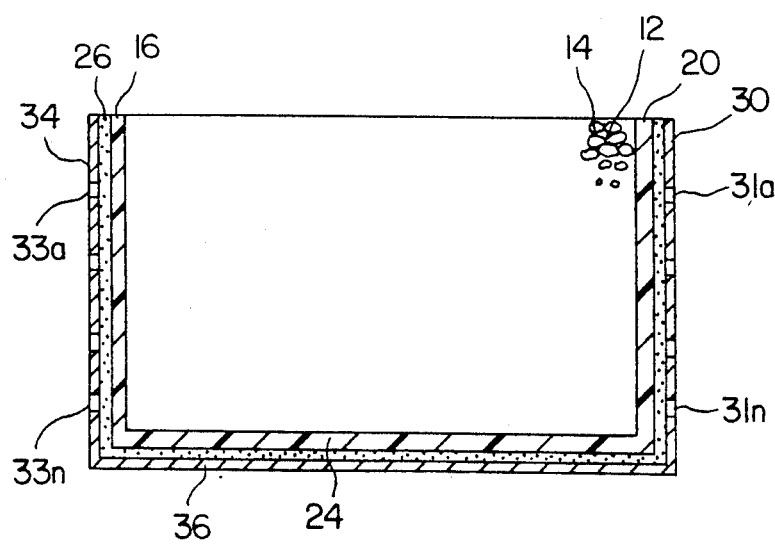
FIG. 2 illustrates a conceptual side view.

FIG. 2 illustrates a conceptual side view in cross section of FIG. where all numerals correspond to those elements previously described.

MODE OF OPERATION

Figure 3:
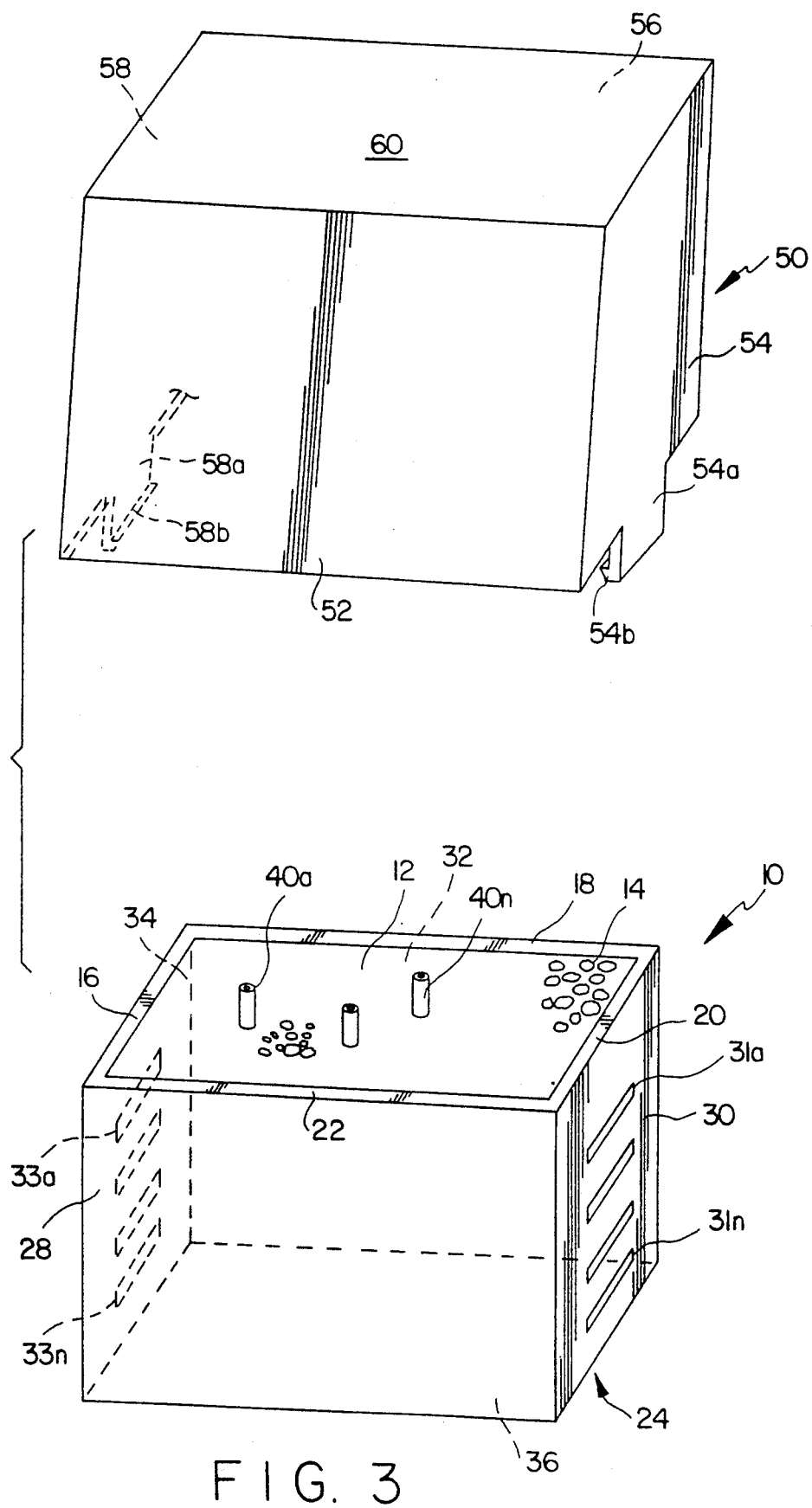
FIG. 3 illustrates an optional top for engagement to a package with needles for disposal.

FIG. 3 illustrates a plurality of needles 40a-40n engaged into the STYROFOAM 14 in the package 10. A plurality of needles can be placed into the package 10 until either one makes a decision to dispose of the package, or in the alternative, the package is full of needles and can no longer accommodate any other needles for disposition. An optional top 50 with four hard sides 52, 54, 56, 58, and a hard top 60 can be engaged over the package 10 and snapped into position so that the bottom and top cannot be separated at a later time. Sides 58 and 54 include extension members 58a and 54a extending downwardly and having locking tab members 58b and 54b located respectively at the lower edges to engage corresponding latching groove members contained in a plurality of latching grooves 31a-31n on side 20 and a plurality of latching grooves 33a-33n on side 16. Cutouts in the double-sided sticky tape and associated peel-away coverings align with the latching grooves 31a-31n and 33a-33n to accommodate the locking tab members 54b and 58b. The extension members 54a and 58a can also extend beyond the plurality of latching grooves 31a-31n and 33a-33n and snappingly engage the lower edge of sides 16 and 20 to lock the top 50 over and about the top portion of the medical needle disposal package 10. The use of pluralities of latching grooves allows the package 10 and top 50 to accommodate needles or other sharp surgical devices of varying heights.

Engaging locks or clips can be alternatively provided internally for the package top and bottom for engaging with respect to each other.

The package 10 can later be disposed by accepted contaminated surgical waste procedures, such as incinerators or landfills.

DESCRIPTION OF AN ALTERNATIVE EMBODIMENT

Figure 4:
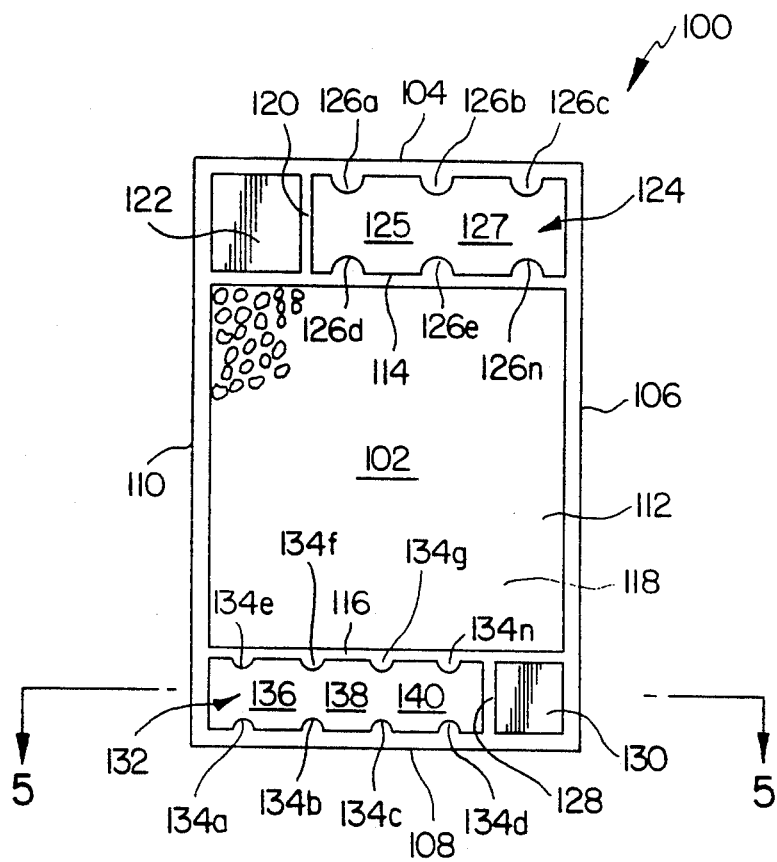
FIG. 4, an alternative embodiment, illustrates a top view of the medical disposal package.
Figure 6:
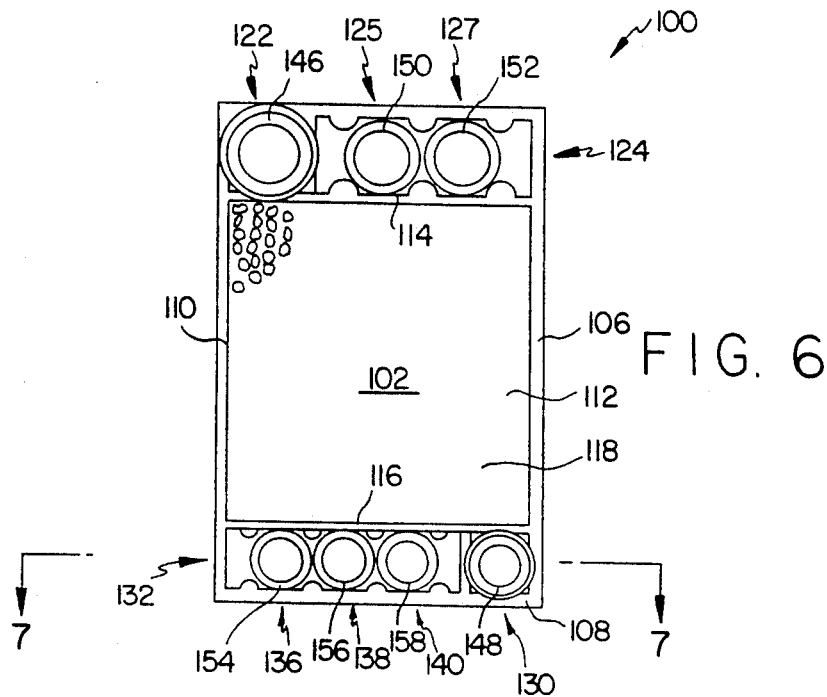
FIG. 6 illustrates a top view of the medical disposal package engaging a number of devices.

FIG. 4, an alternative embodiment, illustrates a top view of a medical disposal package 100 including a compartmented block or like member 102 of soft or pliable cellular material such as STYROFOAM, by way of example and for purposes of illustration only and not to be construed as limiting of the present invention, surrounded by various compartments and planar side members. Hard planar side walls 104, 106, 108 and 110 and a bottom 112 form the outer structure for the medical disposal package 100. Intermediate hard walls 114 and 116, being of a lesser thickness than side walls 104-110 and bottom 112, extend between hard walls 106 and 110 to form a central compartment 118 for the containment of the STYROFOAM 102. A shorter intermediate hard wall 120 extends between the planar hard walls 114 and 104 to form a square compartment 122 comprised of portions of walls 104, 110, 114 and 120 and bottom 112. An elongated compartment 124 is comprised of portions of walls 104, 106, 114, 120 and bottom 112. The square compartment 122 generally is for engagement of a needle cap whether of round construction or round construction with spaced ridges. A plurality of vertically oriented ridges 126a-126n are integral parts of the walls 104 and 114, as illustrated. Sets of ridges, such as 126a, 126b, 126d, 126e or 126b, 126c, 126e and 126n form capture areas 125 and 127 for containment of cylindrical shaped needle sheaths as illustrated in FIG. 6. In a similar fashion another short intermediate hard wall 128 extends between the planar hard walls 108 and 116 to form a square compartment 130 for engagement of round caps or round constructed caps with spaced ridges and is comprised of portions of walls 108, 110, 116, 128 and bottom 112. An elongated compartment 132 is comprised of portions of walls 108, 110, 116, 128 and bottom 112. A plurality of vertically oriented ridges 134a-134n are integral parts of the walls 108 and 112 as illustrated. Sets of ridges such as 134a, 134b, 134e and 134f and the like form capture areas 136, 138 and 140 for the frictional engagement of needle sheaths. Although the compartments 122, 124, 130 and 132 are vertically aligned with respect to the central compartment 118, they can also be constructed at another angle differing from vertical alignment, such as, but not limited to, a 30°, 60°, or 90° angle. It is also appreciated that the compartments can also be reusable and separate from the area containing a disposable STYROFOAM block.

Figure 5:
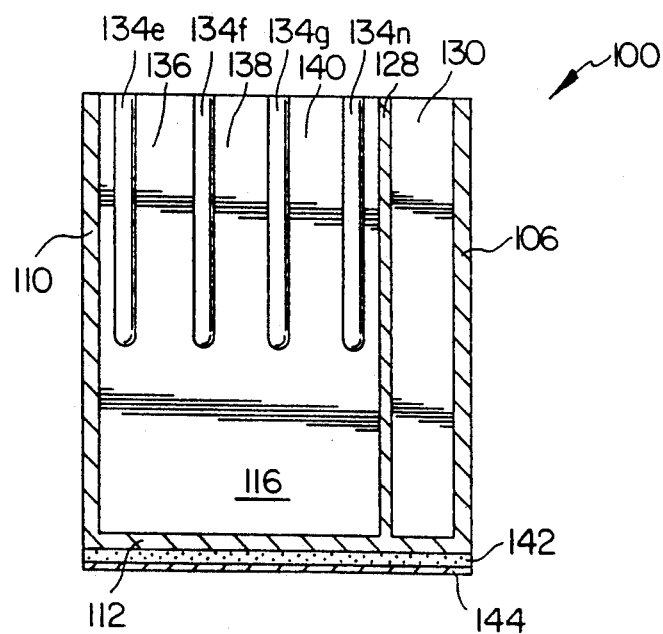
FIG. 5 illustrates a cross-sectional view along line 5—5 of FIG. 4.

FIG. 5 illustrates a cross-sectional view along line 5—5 of FIG. 4 where all numerals correspond to those elements previously described. Also illustrated is a sticky tape surface 142 and peel-away covering 144 which is used to adhesively engage the medical disposal package 100 to a medical tray.

FIG. 6 illustrates a top view of the medical disposal package 100 engaging a number of devices including sheaths and needle caps where all numerals correspond to those elements previously described. Needle caps 146 and 148 engage square compartments 122 and 130, respectively. Needle sheaths 150 and 152 are illustrated in frictional engagement in capture areas 125 and 127, thus causing the thinly constructed wall 114 to expand inwardly as illustrated against and compressing the STYROFOAM block 102 causing STYROFOAM compaction. Needle sheaths 154, 156 and 158 are illustrated in frictional engagement in capture areas 136, 138 and 140, thus causing the thinly constructed wall 116 to expand inwardly as illustrated against and compressing the STYROFOAM block 102 causing STYROFOAM compaction, as well as by frictional engagement of the sheaths or caps. Also, the compressed STYROFOAM further engages by frictional engagement the sharps.

Figure 7:
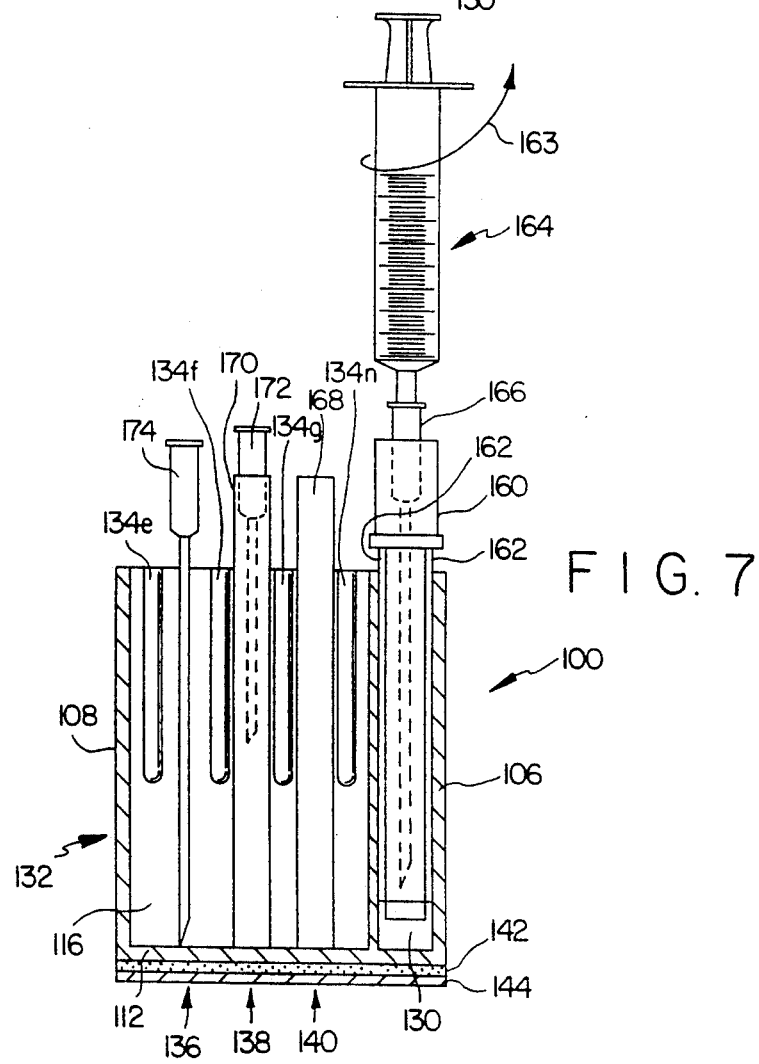
FIG. 7 illustrates a cross-sectional view of a compartment along line 7—7 of FIG. 6.

FIG. 7 illustrates a cross-sectional view of the compartments 108 and 132 along line 7—7 of FIG. 6 and including different medical items aligned therein. All other numerals correspond to those elements previously described. A needle cap of round construction and having spaced ridges 162 is illustrated in engagement with the square compartment 130. The spaced ridges 162 engage the corner of the square compartment 130 to prevent turning or twisting of the needle cap 160 within the square compartment 130. A syringe 164 and needle 166 are illustrated in engagement with the needle cap 160. A twisting and upward movement of the syringe with one hand as illustrated by arrow 163 serves to disengage the syringe and needle from the needle cap 160.

A needle sheath 168 is frictionally engaged in the capture area 140. Another needle sheath 170 is frictionally engaged in the capture area 138. A needle 172 of shorter stature, possibly for another specific use, is frictionally engaged in the sheath 170 awaiting use via engagement by a syringe such as syringe 164 or other syringe (not illustrated). A needle 174 awaits use in capture area 136.

Figure 8:
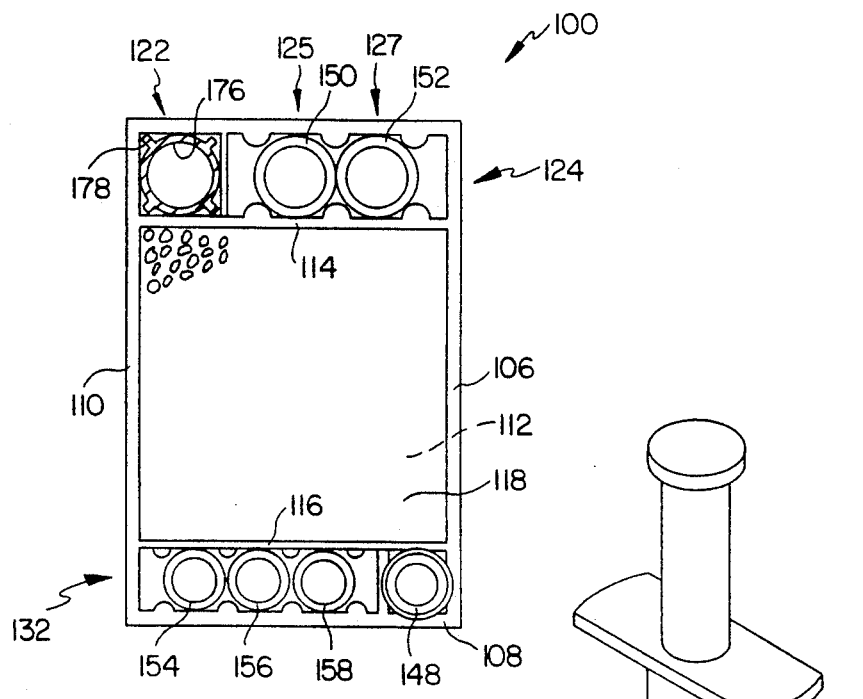
FIG. 8 illustrates a top view of the medical disposal package.

FIG. 8 illustrates a top view of the medical disposal package 100 similar to FIG. 6, but illustrating a cross section horizontally along needle cap 176 engaged in the square compartment 122. The cap 176 includes aligned and spaced ridges 178 about its periphery which engage the corners of the square compartment 122 to prevent twisting of the cap 176 during one-handed removal of a needle and syringe.

Figure 9:
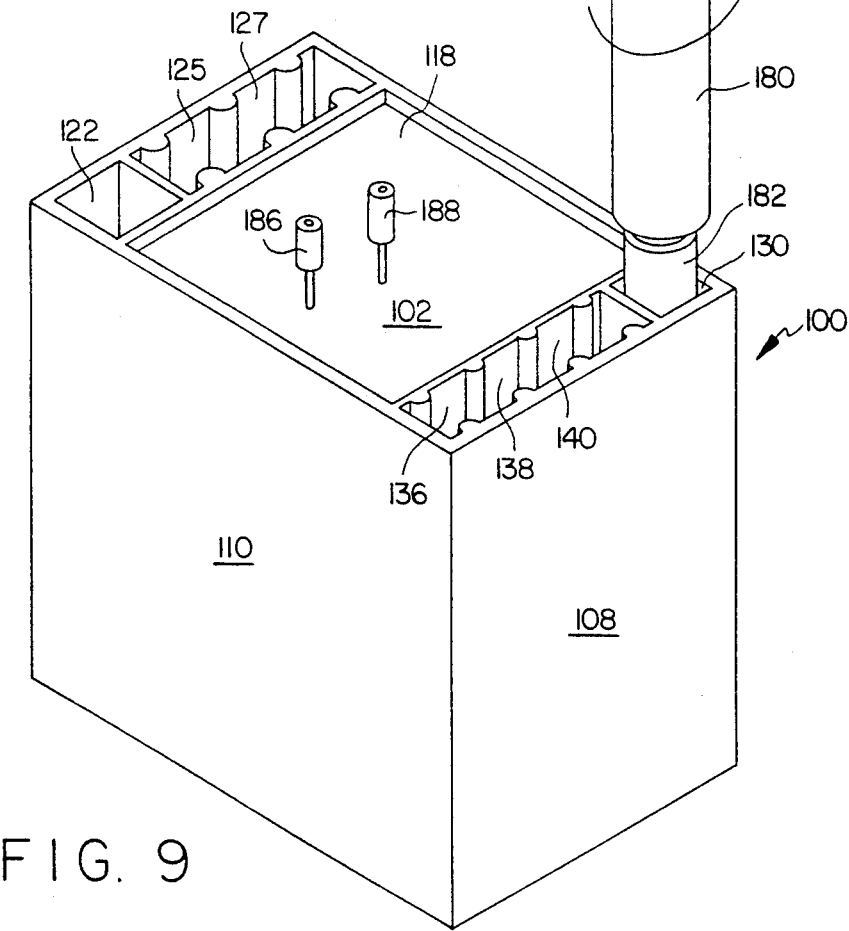
FIG. 9 illustrates a syringe and needle engaged in a compartment.

FIG. 9 illustrates a syringe 180 and needle cap 182 engaged in the square compartment 130 of the medical disposal package 100. All other numerals correspond to those elements previously described. A simple one-handed upward twist as illustrated by arrow 184 disengages the syringe 180 from the cap 182 for use during a procedure. Several spent needles 186 and 188 are illustrated buried in the STYROFOAM block 102.

Figure 10:
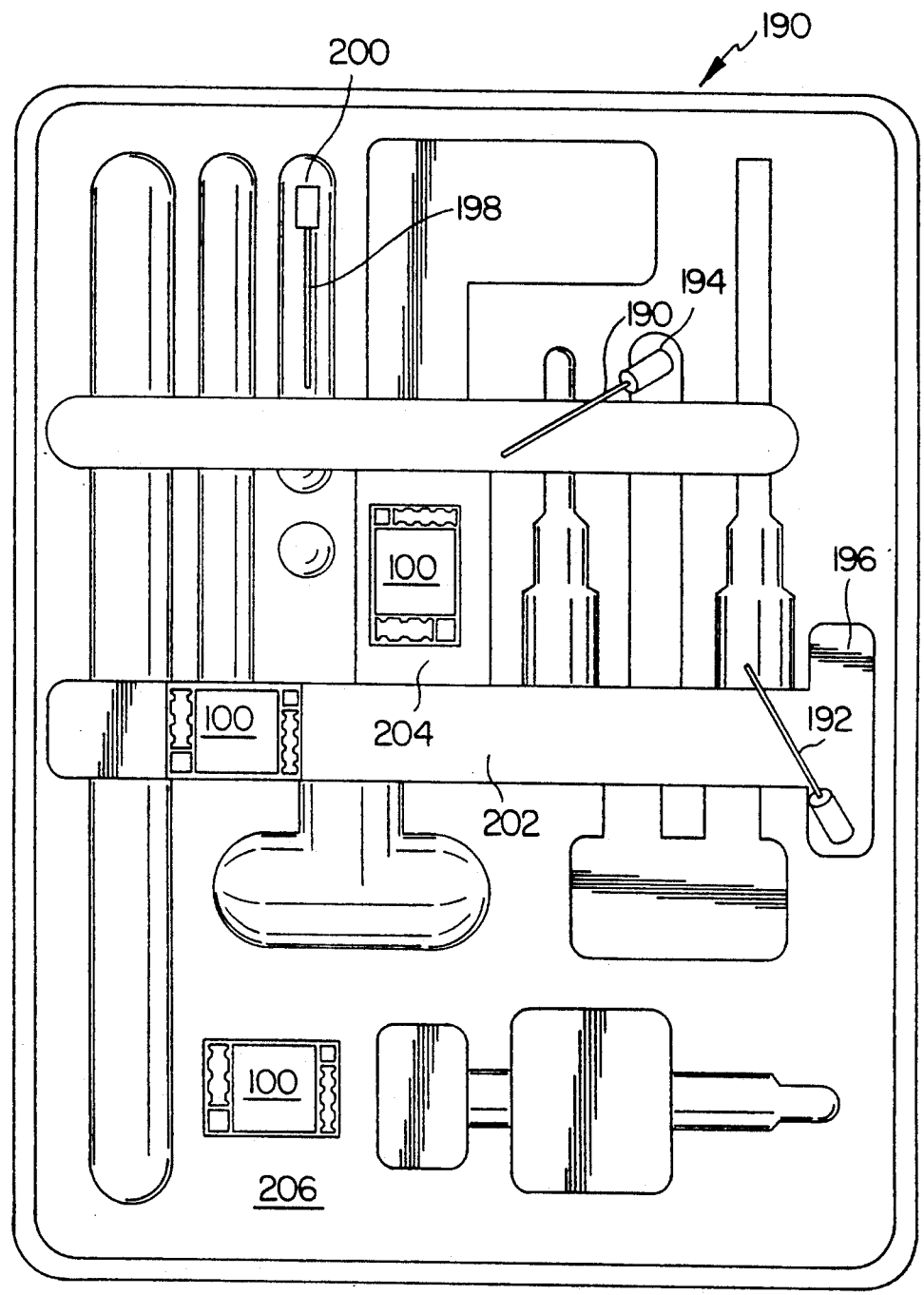
FIG. 10 illustrates the use of several of the medical disposal packages on a surgical tray.

FIG. 10 illustrates the use of several of the medical disposal packages 100 used on a surgical tray 190. All other numerals correspond to those elements previously described. Needles 190 and 192 are shown distributed carelessly within the tray compartments 194 and 196 and aligned at various angles, thus posing a potential of coming in skin puncturing contact with the user using devices in the tray. Another needle 198 which could also be any other desired surgical device, is carelessly aligned in a tray compartment 200. Retrieval of the needle 198 from the tray compartment 200 is difficult at best. Storage of the needles 190, 192 and 198 in any of the medical disposal packages 100 found in tray compartments 202 and 204 or on an upper planar surface 206 alleviates the problem of user hand puncture or sharps retrieval.

Figure 11:
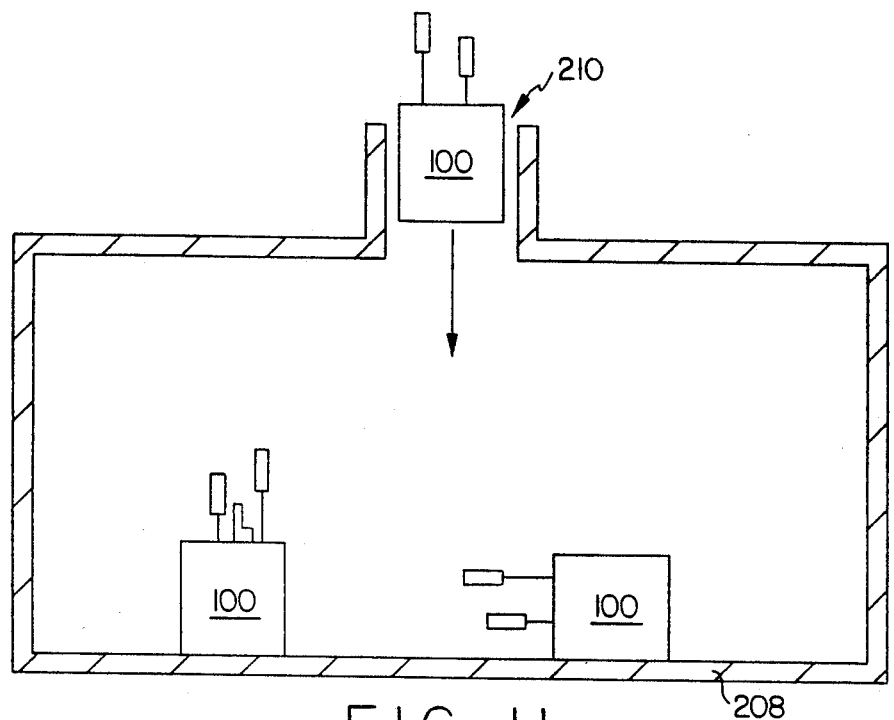
FIG. 11 illustrates methods of disposal of the medical disposal package.

FIG. 11 illustrates a disposal method for the medical disposal packages 100 including spent sharps deposited within. A disposal container 208 having an upper opening 210 is used to collect and collectively dispose of spent sharps.

Figure 12:
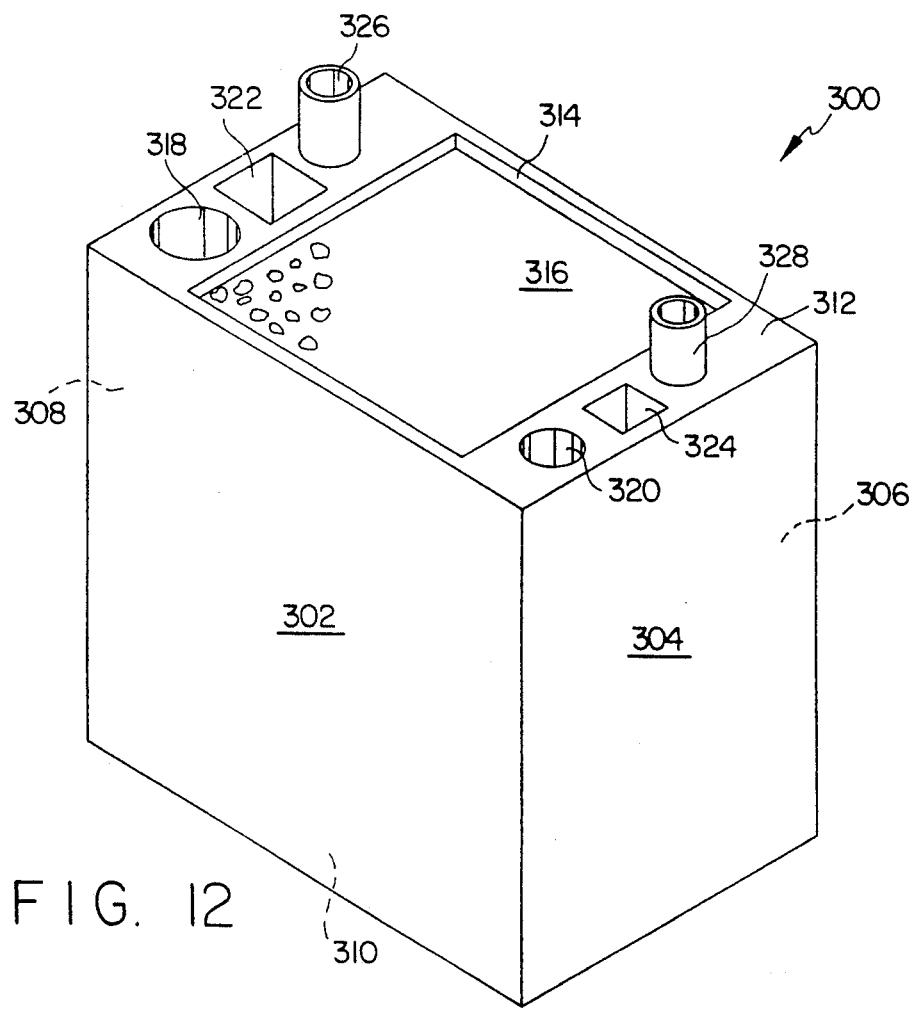
FIG. 12, an alternative embodiment, illustrates a medical disposal package have integral built-in compartments.

FIG. 12, an alternative embodiment, illustrates a medical disposal package 300 similar in many aspects to the medical disposal package 100, but having integral built-in compartments to simulate and approximate the interiors of needle caps and sheaths. The package 300 includes sides 302, 304, 306 and 308 and a bottom surface 310. Extending downwardly from the top surface 312 is a compartment 314 for containment of a STYROFOAM block 316 for containment of used sharps. The outer portions of the top surface 312 include an integral cap compartment 318 having an internal shape similar to that of the internal shape of a needle cap. Another integral needle cap compartment 320 having different internal dimensions and having the internal shape of a needle cap aligns on the opposing surface portion of the top surface 312. Opposing square compartments 322 and 324, each of different dimensions, are also included for engagement of needle caps. Integral sheaths 326 and 328 of different dimensions are located at opposite portions of the upper surface 312 for storage of needles. The interior of the integral sheaths 326 and 328 have an internal shape and dimension replicating that of a needle sheath.

Various modifications can be made to the present invention without departing from the apparent scope hereof. The physical sizes and compartments can be variable to accommodate sharps for specific procedures and/or specific sharps. A sterile packaged kit can be provided with the package and such as a syringe with a local anesthetic and needle, and an IV needle.

I claim:

1. Medical disposal package comprising:
   a. a four-sided package with a bottom;
   b. at least one inside compartment wall, said inside compartment wall having a first side defining a large compartment and a second side defining at least one small compartment, said second side having a plurality of ridges for engagement of a needle cap or a sheath in said at least one small compartment; and,
   c. expanded polystyrene in said large compartment.

2. The package of claim 1 including sticky means on a bottom of said container.

3. The package of claim 1, further comprising a plurality of sharps secured in said expanded polystyrene.

4. The package of claim 3, wherein said sharps are needles.

5. The package of claim 3, wherein said sharps are lancets.

6. The package of claim 3, wherein said sharps are knives.

7. The package of claim 1 in a color coded color.

8. Medical disposal package comprising:
   a. a four-walled package with a bottom;
   b. at least one inside compartment wall, said inside compartment wall having a first side defining a large compartment and a second side defining at least one small compartment, said second side having a plurality of ridges for engagement of a needle cap or a sheath in said at least one small compartment, said inside compartment wall having a thickness less than the thickness of each of said four walls of said package so as to allow for movement during said engagement; and,
   c. expanded polystyrene in said large compartment.

9. The package of claim 8 including sticky means on a bottom of said container.

10. The package of claim 8, further comprising a plurality of sharps secured in said expanded polystyrene.

11. The package of claim 8, wherein said sharps are needles.

12. The package of claim 8, wherein said sharps are lancets.

13. The package of claim 8, wherein said sharps are knives.

14. The package of claim 8 in a color coded color.

15. Medical disposal package comprising:
 a. a four-sided package with a bottom;
 b. a large compartment and at least one small compartment in said package, said at least one small compartment having a plurality of ridges for engaging a needle cap or a sheath in said small compartment;
 c. expanded polystyrene in said large compartment; and,
 d. at least one needle cap or sheath molded into said package.

16. The package of claim 15 including sticky means on a bottom of said container.

17. The package of claim 15, further comprising a plurality of sharps secured in said expanded polystyrene.

18. The package of claim 15, wherein said sharps are needles.

19. The package of claim 15, wherein said sharps are lancets.

20. The package of claim 15, wherein said sharps are knives.

* * * * *